US012714571B2

(12) United States Patent
Roeder et al.

(10) Patent No.: US 12,714,571 B2
(45) **Date of Patent: *Aug. 25, 2026**

(54) POROUS COMPOSITE BIOMATERIALS AND RELATED METHODS

(71) Applicant: HAPPE SPINE, LLC, Grand Rapids, MI (US)

(72) Inventors: Ryan K. Roeder, Granger, IN (US); Gabriel L. Converse, Basehor, KS (US); Stephen M. Smith, South Bend, IN (US)

(73) Assignee: HAPPE SPINE, LLC, Grand Rapids, MI (US)

( * ) Notice: Subject to any disclaimer, the term of this patent is extended or adjusted under 35 U.S.C. 154(b) by 256 days.

This patent is subject to a terminal disclaimer.

(21) Appl. No.: 18/750,616

(22) Filed: Jun. 21, 2024

(65) Prior Publication Data

US 2024/0341972 A1 Oct. 17, 2024

Related U.S. Application Data

(63) Continuation of application No. 17/519,336, filed on Nov. 4, 2021, now Pat. No. 12,048,633, which is a continuation of application No. 17/180,935, filed on Feb. 22, 2021, now abandoned, which is a continuation of application No. 14/078,614, filed on Nov. 13, 2013, now Pat. No. 10,945,854, which is a (Continued)

(51) Int. Cl.

| | |
|---|---|
| ***A61F 2/44*** | (2006.01) |
| ***A61F 2/28*** | (2006.01) |
| ***A61L 27/12*** | (2006.01) |
| ***A61L 27/18*** | (2006.01) |
| ***A61L 27/26*** | (2006.01) |
| ***A61L 27/46*** | (2006.01) |
| ***A61L 27/54*** | (2006.01) |
| ***A61L 27/56*** | (2006.01) |
| ***B29C 67/20*** | (2006.01) |
| ***C08J 9/00*** | (2006.01) |
| ***C08J 9/28*** | (2006.01) |
| ***C08J 9/36*** | (2006.01) |
| *A61F 2/30* | (2006.01) |

(52) U.S. Cl.

CPC .............. *A61F 2/4455* (2013.01); *A61F 2/28* (2013.01); *A61F 2/4465* (2013.01); *A61L 27/12* (2013.01); *A61L 27/18* (2013.01); *A61L 27/26* (2013.01); *A61L 27/46* (2013.01); *A61L 27/54* (2013.01); *A61L 27/56* (2013.01); *B29C 67/202* (2013.01); *C08J 9/0066* (2013.01); *C08J 9/28* (2013.01); *C08J 9/36* (2013.01); *A61F 2002/2817* (2013.01); *A61F 2002/2835* (2013.01); *A61F 2002/30006* (2013.01); *A61F 2002/30011* (2013.01); *A61F 2002/30032* (2013.01); *A61F 2002/30062* (2013.01); *A61F 2002/30065* (2013.01); *A61F 2002/30225* (2013.01); *A61F 2002/30235* (2013.01); *A61F 2002/30622* (2013.01); *A61F 2002/30904* (2013.01); *A61F 2002/3092* (2013.01); *A61F 2002/30957* (2013.01); *A61F 2/30965* (2013.01); *A61F 2210/0004* (2013.01); *A61F 2210/0071* (2013.01); *A61F 2230/0069* (2013.01); *A61F 2250/0015* (2013.01); *A61F 2250/0018* (2013.01); *A61F 2250/0023* (2013.01); *A61F 2250/0031* (2013.01)

(58) Field of Classification Search

None

See application file for complete search history.

(56) References Cited

U.S. PATENT DOCUMENTS

| | | | |
|---|---|---|---|
| 6,149,688 | A | 11/2000 | Brosnahan et al. |
| 6,887,408 | B2 | 5/2005 | Yuan |

(Continued)

FOREIGN PATENT DOCUMENTS

| | | | |
|---|---|---|---|
| WO | 2001054746 | A2 | 8/2001 |
| WO | 2005047467 | A2 | 5/2005 |

(Continued)

OTHER PUBLICATIONS

Rotel, M., et al., Preadhesion Laser Surface Treatment of Carbon Fiber Reinforced PEEK Composite; A. Buchman & H. Dodiuk; Dec. 1995.

(Continued)

*Primary Examiner* — David J Blanchard
*Assistant Examiner* — Daniel F Coughlin
(74) *Attorney, Agent, or Firm* — McNees Wallace & Nurick LLC

(57) ABSTRACT

A composite material for use, for example, as an orthopedic implant, that includes a porous reinforced composite scaffold that includes a polymer, reinforcement particles distributed throughout the polymer, and a substantially continuously interconnected plurality of pores that are distributed throughout the polymer, each of the pores in the plurality of pores defined by voids interconnected by struts, each pore void having a size within a range from about 10 to 500 μm. The porous reinforced composite scaffold has a scaffold volume that includes a material volume defined by the polymer and the reinforcement particles, and a pore volume defined by the plurality of pores. The reinforcement particles are both embedded within the polymer and exposed on the struts within the pore voids. The polymer may be a polyaryletherketone polymer and the reinforcement particles may be anisometric calcium phosphate particles.

20 Claims, 6 Drawing Sheets

Related U.S. Application Data continuation of application No. 12/039,666, filed on Feb. 28, 2008, now abandoned.

(60) Provisional application No. 60/939,256, filed on May 21, 2007, provisional application No. 60/904,098, filed on Feb. 28, 2007.

(56) References Cited

U.S. PATENT DOCUMENTS

| | | | |
|---|---|---|---|
| 7,758,882 | B2 | 7/2010 | Roeder et al. |
| 7,879,093 | B2 | 2/2011 | Wei et al. |
| 7,972,628 | B2 | 7/2011 | Ratner et al. |
| 8,318,193 | B2 | 11/2012 | Ratner et al. |
| 8,383,024 | B2 | 2/2013 | Morrissette et al. |
| 8,530,560 | B2 | 9/2013 | Kerr et al. |
| 8,609,127 | B2 | 12/2013 | Savage-Erickson |
| 8,729,150 | B2 | 5/2014 | Jarman-Smith et al. |
| 8,829,096 | B2 | 9/2014 | Jarman-Smith |
| 2002/0115742 | A1 | 8/2002 | Trieu et al. |
| 2003/0031698 | A1 | 2/2003 | Roeder et al. |
| 2005/0100578 | A1 | 5/2005 | Schmid et al. |
| 2005/0112397 | A1 | 5/2005 | Rolfe et al. |
| 2005/0251267 | A1 | 11/2005 | Winterbottom et al. |
| 2007/0041952 | A1 | 2/2007 | Guilak et al. |
| 2008/0161927 | A1 | 7/2008 | Savage et al. |
| 2008/0206297 | A1 | 8/2008 | Roeder et al. |
| 2009/0164023 | A1 | 6/2009 | Devine |
| 2009/0317766 | A1 | 12/2009 | Heidenau et al. |
| 2010/0016985 | A1 | 1/2010 | Rebiei |
| 2010/0129416 | A1 | 5/2010 | Murphy et al. |
| 2010/0145393 | A1 | 6/2010 | Fallin et al. |
| 2010/0168798 | A1 | 7/2010 | Clineff et al. |
| 2010/0211183 | A1 | 8/2010 | Chi |
| 2010/0298937 | A1 | 11/2010 | Laurencin et al. |
| 2010/0317039 | A1 | 12/2010 | Salk et al. |
| 2011/0012280 | A1 | 1/2011 | Deslauriers et al. |
| 2011/0022180 | A1 | 1/2011 | Melkent et al. |
| 2011/0022181 | A1 | 1/2011 | Kasahara et al. |
| 2011/0035018 | A1 | 2/2011 | Deffenbaugh et al. |
| 2011/0045087 | A1 | 2/2011 | Kerr et al. |
| 2011/0054625 | A1 | 3/2011 | Ferko et al. |
| 2011/0151259 | A1 | 6/2011 | Jarman-Smith et al. |
| 2011/0189466 | A1 | 8/2011 | Jaggi et al. |
| 2011/0230590 | A1 | 9/2011 | Jarman-Smith et al. |
| 2012/0101185 | A1 | 4/2012 | Valentine et al. |
| 2012/0185047 | A1 | 7/2012 | Wooley |
| 2012/0323339 | A1 | 12/2012 | Graells et al. |
| 2013/0066320 | A1 | 3/2013 | Jarman-Smith et al. |
| 2013/0171443 | A1 | 7/2013 | Morrissette et al. |
| 2014/0035201 | A1 | 2/2014 | Jarman-Smith et al. |
| 2014/0107299 | A1 | 4/2014 | Valentine et al. |
| 2014/0200466 | A1 | 7/2014 | Sereno et al. |
| 2014/0228497 | A1 | 8/2014 | Jarman-Smith |
| 2014/0343707 | A1 | 11/2014 | Sereno et al. |

FOREIGN PATENT DOCUMENTS

| | | | |
|---|---|---|---|
| WO | 2008106625 | A3 | 9/2008 |
| WO | 2013076493 | A1 | 5/2013 |
| WO | 2014068285 | A1 | 5/2014 |

OTHER PUBLICATIONS

Kausch, H., et al., Advanced Thermoplastic Composites: Characterization and Processing; Oxford University Press, USA, 1993, p. 341.

R.J. Kane, G.L. Converse and R.K. Roeder, "Effects of the reinforcement morphology on the fatigue properties of hydroxyapatite reinforced polymers," J. Mech. Behav. Biomed. Mater., 1 [3] 261-268 (2008).

Dalby, M.J., et al., Surface topography and HA filler volume effect on primary human osteoblasts in vitro., Bonfield W.J Mater Sci Mater Med. Dec. 2000;11(12):805-10.

D.W. Grant, "Reduced Burst Release of Bioactive rhBMP-2 from a Three-Phase Composite Scaffold," M.S. Thesis, University of Toronto, 2010.

Lickorish, D., et al., A three-phase, fully resorbable, polyester/calcium phosphate scaffold for bone tissue engineering: Evolution of scaffold design; Elsevier, Science Direct, Biomaterials 28 (2007) 1495-1502, Canada.

Kurtz, S., et al., PEEK biomaterials in trauma, orthopedic, and spinal implants; Elsevier, Science Direct, Biomaterials 28 (2007) 4845-4869.

Ishaug, et al; Bone formation by three-dimensional stromal osteoblast culture in biodegradable polymer scaffolds; Journal of Biomedical Materials Research, vol. 36, 17-28 (1997).

Thomson, et al; Hydroxyapatite bber reinforced poly(a-hydroxy ester) foams for bone regeneration; Biomaterials 19 (1998) 1935D1943.

Chawla, Krishan K., Composite Materials, Science and Engineering, Second Edition, 1998, 1987 Springer Science + Business Media, Inc., United States.

Post, M.J. "Design and Manufacture of Polymer Osseointegrative Scaffolds," Graduate Program in Aerospace and Mechanical Engineering, Notre Dame, IN, 2007.

Schmid, S.R., et al., "A Manufacturing Framework for Biomimetic Porous Metals," Department of Aerospace and Mechanical Engineering, University of Notre Dame, IN. Transactions of NAMRI/SME, pp. 183-188, vol. 37, 2009.

Tan, K.H., et al., "Fabrication and characterization of three-dimensional poly(ether-ether-ketone)/-hydroxyapatite biocomposite scaffolds using laser sintering." 2004, pp. 183-194, Proc. IMechE. vol. 219 Part H: J. Engineering in Medicine, 2004.

Tan, K.H., et al., "Selective Laser sintering of biocompatible polymers for applications in tissue engineering." Bio- Medical Materials and Engineering 15 (2005) pp. 113-124. 2005-IOS Press.

Von Wilmowsky, C., et al., "Effects of bioactive glass and ß-TCP containing three-dimensional laser sintered polyetheretherketone composites on osteoblasts in vitro." Wiley Periodicals, Inc. J. Biomed Mater Res 87A: 896-902, 2008.

Duan, B. et al., "Three-dimensional nanocomposite scaffolds fabricated via selective laser sintering for bone tissue engineering." Acta Biomaterialia 6 (2010) 4495-4505, Elsevier Ltd.

Evans, N.T., et al., "High-strength, surface-porous polyether-ether-ketone for load-bearing orthopedic implants." Acta Biomaterialia 13 (2015) 159-167, Elsevier Ltd.

Siddiq, A.R., et al., "Porous poly-ether ether ketone (PEEK) manufactured by a novel powder route using near-spherical salt bead porogens: Characterisation and mechanical properties." Materials Science and Engineering C 47 (2015) 180-188, 2014 Elsevier B.V.

Evans, N.T., et al., "Impact of surface porosity and topography on the mechanical behavior of high strength biomedical polymers." Journal of the Mechanical Behavior of Biomedical Materials 59 (2016) 459-473, 2016 Elsevier Ltd.

P. Moreno, Femtosecond laster ablation of carbon reinforced polymers, Applied Surface Science 252 (2006) 4110-4119; Elsevier B.V.

R. Roeder et al., Porous and Bioactive PEEK Implants for Interbody Spinal Fusion, Advanced Materials & Processes, Oct. 2009.

R. Roeder et al., Hydroxyapatite-Reinforced Polymer Biocomposites for Synthetic Bone Substitutes, Mar. 2008, JOM, pp. 38-45.

G. Converse et al., Mechanical properties of hydroxyapatite whisker reinforced polyetherketoneketone composite scaffolds, Journal of Mechanical Behavior of Biomedical Materials 2 (2009) 627-635, Elsevier B.V.

G. Converse et al., Hydroxyapatite whisker-reinforced polyetherketoneketone bone ingrowth scaffolds, Acta Biomaterialia 6(2010) 856-863; Elsevier B.V.

J. Deuerling et al., Micromechanical Model for the Orthotropic Elastic Constants of Polyetheretherketone Composites Considering the Orientation Distribution of the Hydroxyapatite Whisker Reinforcements; Journal of Engineering Materials and Technology, Jan. 2012, vol. 134, pp. 010906-1-8.

R. Roeder et al., Bioactive Polyaryletherketone Composites, PEEK Biomaterials Handbook, 2012, Chapter 11, pp. 163-179; Elsevier B.V.

(56) References Cited

OTHER PUBLICATIONS

T. Conrad et al., Effects of the mold temperature on the mechanical properties and crystallinity of hydroxyapatite whisker-reinforced polyetheretherketone scaffolds; Journal of Biomedical Materials Reserach B: Applied Biomaterials, May 2013, vol. 101B, issue 4, pp. 576-583; Wiley Periodicals, Inc.

M. Meagher et al., Surface Adsorption of rhBMP-2 to Hydroxyapatite Reinforced PEEK Scaffolds, Abstract; Department of Aerospace and Mechanical Engineering, Bioengineering Graduate Program, University of Notre Dame.

PCT Notification of Transmittal of the International Search Report and the Written Opinion of the International Searching Authority, or the Declaration for Application No. PCT/US2020/022468 dated Jun. 30, 2020.

Goldstein, "The Mechanical Properties of Trabecular Bone Dependent on Anatomic Location and Function," J. Biomechanics, vol. 20, No. 11, p. 1055-1066, 1987.

Karageorgiou et al., "Porosity of 3D biomaterial scaffolds and osteogenesis," Biomaterials 26: 5474-5491, 2005.

Merriam-Webster, retrieved Oct. 24, 2022, https:www.merriam-webster.com/-dictionary/trapped.

POROUS COMPOSITE BIOMATERIALS AND RELATED METHODS

PRIORITY CLAIM/RELATED APPLICATIONS

This application is a continuation of and claims priority to U.S. patent application Ser. No. 17/519,336, filed on Nov. 4, 2021, entitled "Porous Composite Biomaterials and Related Methods," which is a continuation of and claims priority to U.S. patent application Ser. No. 17/180,935, filed on Feb. 22, 2021, entitled "Porous Composite Biomaterials and Related Methods," which is a continuation of and claims priority to U.S. patent application Ser. No. 14/078,614, filed on Nov. 13, 2013, entitled "Porous Composite Biomaterials and Related Methods," now patented as U.S. Pat. No. 10,945,854, which is a continuation of U.S. patent application Ser. No. 12/039,666, filed on Feb. 28, 2008, entitled "Porous Composite Biomaterials and Related Methods," which claims the benefit of U.S. Provisional Patent Application Ser. No. 60/904,098, filed on Feb. 28, 2007, entitled "Reinforced Porous Polymer Scaffolds," and U.S. Provisional Patent Application Ser. No. 60/939,256, filed on May 21, 2007, entitled "Interbody Spinal Fusion Cages Containing Anisometric Calcium Phosphate Reinforcements and Related Methods," each of which is incorporated herein by reference in its entirety. This Application is also related to U.S. patent application Ser. No. 16/134,453, filed on Sep. 18, 2018, entitled "Implantable Devices" which has issued as U.S. Pat. No. 11,179,243 as of Nov. 23, 2021, which claims priority to U.S. patent application Ser. No. 14/078,614 which is a continuation of and claims priority to U.S. patent application Ser. No. 12/039,666 which claims the benefit of U.S. Provisional Patent Application Ser. No. 60/904,098, filed on Feb. 28, 2007 and 60/939,256, filed on May 21, 2007 all of which are incorporated herein in their entireties.

FIELD OF THE DISCLOSURE

The present disclosure relates generally to composite biomaterials and more particularly to porous composite biomaterials and related methods.

BACKGROUND

Natural bone grafts such as autogenous bone grafts (autografts) are commonly used in procedures for repairing or replacing bone defects because they provide good structural support and osteoinductivity. Natural bone grafts involve removing or harvesting tissue from another part of a host's body (e.g., typically from the iliac crest, hip, ribs, etc.) and implanting the harvested tissue in the defect site. Not only do these grafts require an added surgical procedure needed to harvest the bone tissue, these grafts have limitations, including for example, transplant site morbidity. One alternative to autografts is allografts, which involve removing and transplanting tissue from another human (e.g., from bone banks that harvest bone tissue from cadavers) to the defect site. However, allografts are known to induce infection and immunotoxicity, suffer from limited supply and variability, and have a lessened effectiveness because the cells and proteins that promote bone growth are lost during the harvesting process (e.g., during cleansing and disinfecting process). Demineralized bone matrix (DBM) is typically used to induce bone growth at defect sites, but DBM lacks the mechanical properties (e.g., stiffness, strength, toughness, etc.) necessary to be considered a viable option for load-bearing applications.

Synthetic bone substitute materials have been researched in the treatment of diseased bone (e.g., osteoporosis), injured bone (e.g., fractures), or other bone defects in lieu of natural bone grafts. Synthetic bone substitutes are viable alternatives to the more traditional methods described above. However, synthetic substitute materials used to repair diseased bones and joints should function or perform biologically and mechanically (i.e., as the structural support role of the bone itself) by, for example, mimicking the density and overall physical structure of natural bone to provide a framework for ingrowth of new tissue. One type or application of a synthetic bone substitute is a scaffold, which provides support for bone-producing cells. Scaffolds may be biodegradable, which degrade in vivo, or they may be non-biodegradable to provide permanent implant fixation (e.g., spinal fusion cages). In addition, scaffolds are typically biocompatible, and some may be bioactive, bioresorbable, osteoconductive, and/or osteoinductive. The shapeability, deliverability, cost, and ability to match the mechanical properties of the surrounding host tissue are other factors that vary among different types of scaffolds and other bone substitutes.

Problems may arise when there is a mechanical mismatch between the bone substitute and the surrounding tissue. For example, metallic implants and dense ceramics have mechanical properties that are typically an order of magnitude greater than the bone tissue. As a result, a stiff metal bone substitute implant acts to "shield" the adjacent bone tissue from mechanical stresses, resulting in a weakened bone at the bone-implant interface. Furthermore, efforts to utilize porous ceramics or polymer bone cement in place of stiffer materials have been limited. For example, ceramics possess low fracture toughness, thereby making the orthopedic implant brittle (i.e., susceptible to fracture). Polymers are limited by higher compliance and lower strength, thereby limiting their ability to support physiological load levels. Additionally, conventional orthopedic implant biomaterials are not osteoconductive and bioactive, resulting in a lack of bonding between the implant and the peri-implant tissue.

DETAILED DESCRIPTION

Figure 1A:
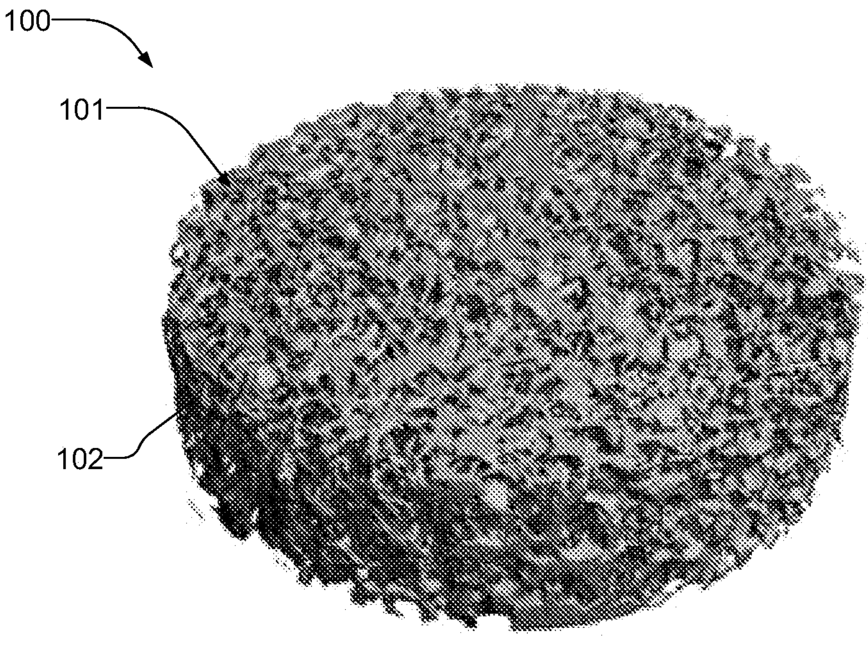
FIG. 1A is a perspective view of an example porous composite material described herein.

In general, the example methods, apparatus, and materials described herein provide a biocompatible, bioactive synthetic porous composite for use as synthetic bone substitute materials. The synthetic composite may provide a synthetic porous scaffold for use an orthopedic implant and/or be injectable via percutaneous or surgical injection to cure in vivo. Because the example composite material is used to form a scaffold or matrix that is used in an implantable device, the descriptions of one or more of these structures may also describe one or more of the other structures. The synthetic porous composites are tailored to mimic biological and mechanical properties of bone tissue for implant fixation, synthetic bone graft substitutes, tissue engineering scaffolds, interbody spinal fusion, or other orthopedic applications. An example porous composite material described herein reduces subsidence and/or bone resorption resulting from mechanical mismatch problems between a synthetic scaffold of an implant device and the peri-implant tissue. Additionally, porosity and/or the pore sizes of the example synthetic composite are tailorable to specific applications to effectively promote the vascularization and growth of bone in the pores and/or void spaces of the example scaffolds, thereby improving bonding between the scaffolds and peri-implant tissue.

The example composite material or scaffolds are synthesized or made through a process that enables reinforcement particles to be integrally formed with or embedded within polymer matrices. In this manner, the polymer matrices embedded with the reinforcement material provide improved material properties (e.g., stiffness, fatigue strength, and toughness). The reinforcement particles are also exposed on a surface of the matrices, which promotes bioactivity and/or bioresorption. Additionally, the process provides flexibility to tailor the level of reinforcement particles and porosity for a desired application. For example, a porogen material may be used to vary the porosity, while the pore size is tailored by, for example, sieving the porogen to a desired size.

By varying the volume of the reinforcement particles and the porosity of the example scaffold, the mechanical properties (e.g., stiffness, strength, toughness, etc.) of the example scaffold of the implant device may be tailored to match those of the adjacent peri-implant bone tissue to reduce mechanical mismatch problems. Reducing mechanical mismatch provides a decreased risk of subsidence, stress shielding, bone resorption, and/or subsequent failure of adjacent peri-implant bone tissue. Additionally, the example scaffold of the implant device may include a significantly high porosity to promote bone ingrowth, while exhibiting significantly higher effective mechanical properties such as, for example, the mechanical properties of trabecular bone.

In particular, the example composite material includes a continuous porous biocompatible matrix having a thermoplastic polymer matrix reinforced with anisometric calcium phosphate particles. More specifically, in one example, a composite material includes a polyetheretherketone (PEEK) or a polyetherketoneketone (PEKK) matrix reinforced with various volume fractions of hydroxyapatite (HA) whiskers (e.g., 20 or 40 volume percent), wherein the matrix is approximately between 70% and 90% porous. In another example, the porous matrix includes a biocompatible, microporous polymer cage reinforced with anisometric calcium phosphate particles and bone morphogenic protein (BMP) such as, for example, rhBMP-2, which can be dispersed or accommodated by the void spaces and/or pores of the example porous scaffold and/or exposed on the surface of the example porous scaffold. Additionally, the BMP binds to the calcium phosphate further localizing the BMP to the surface of the scaffold or matrix.

The example composite materials described herein may be used for applications such as, for example, synthetic bone graft substitutes, bone ingrowth surfaces applied to existing implants, tissue engineering scaffolds, interbody spinal fusion cages, etc. In each of the applications, carrier materials (e.g., collagen, hydrogels, etc.) containing growth factors, such as BMP, may be incorporated into the pore space of the scaffold of the implant device to further enhance osteoinduction and/or osteoconduction to promote osteointegration.

Human bone tissues exhibit substantial variation in mechanical properties depending on the tissue density and microstructure. The properties are highly dependent on anatomic location and apparent density of the measured specimen. For example, a femur includes a cortical bone that has a relative porosity on the order of about 5-15%, and a trabecular bone that has a porosity on the order of about 75-95%. Due to the highly significant porosity differences, the trabecular bone exhibits significantly lower effective mechanical properties compared to the cortical bone. Therefore, depending on the application, synthetic composite materials for use as scaffolds and/or spinal fusion cages or other implant devices should possess the mechanical properties exhibited by the cortical bone or the trabecular bone, but must also have effective porosity to promote bone growth.

To avoid the mechanical mismatch problems, such as stress shielding, the example scaffold of the implant device described herein may be tailored to substantially match or mimic the mechanical properties (e.g., stiffness, strength, toughness, etc.) of the adjacent and/or substituted bone tissue. Several factors may be varied during the synthesis of the composite material and scaffold of the implant device to tailor the mechanical properties including the calcium phosphate reinforcement volume fraction, aspect ratio, size and orientation; the polymer; and the size, volume fraction, shape and directionality of the void space and/or porosity. Tailoring the mechanical properties of the scaffold reduces the likelihood of mechanical mismatch leading to a decreased risk of subsidence, stress shielding, bone resorption and/or subsequent failure of adjacent vertebrae.

Figure 1B:
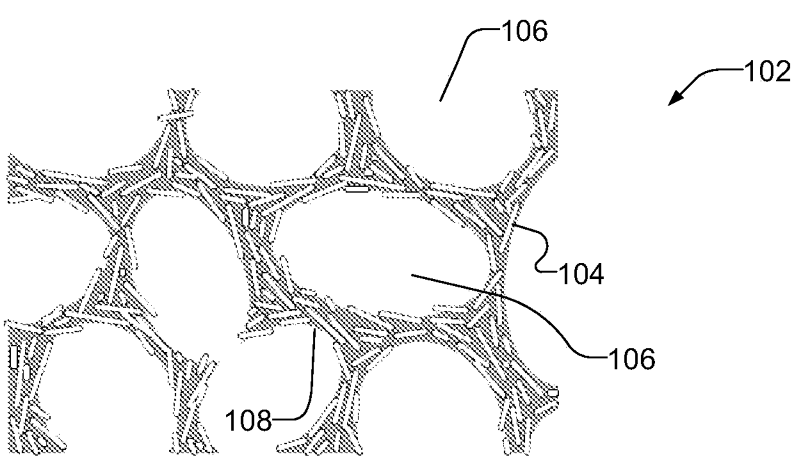
FIG. 1B is a cross-sectional view of a portion of the example porous composite material of FIG. 1A.

FIG. 1A illustrates the example synthetic porous composite material 100 described herein. FIG. 1B is a cross-sectional view of a portion of the example porous composite material 100 of FIG. 1A. The example synthetic composite material 100 provides a synthetic porous scaffold 101 for use or in as an orthopedic implant.

The example synthetic porous composite material 100 includes a porous thermoplastic polymer (e.g., a PEEK polymer) matrix 102 having anisometric calcium phosphate reinforcement particles 104 integrally formed or embedded with the matrix 102 and/or exposed on a surface of the matrix. In this manner, the polymer matrix 102 embedded with the reinforcement particles 104 provides high material strength, and the reinforcement particles 104 exposed on the surface of the matrix 102 promote bioactivity and/or bioresorption. The porous polymer matrix 102 includes a substantially continuous porosity and a plurality of pores 106 to enable bone ingrowth into the porous matrix 102. In addition, the matrix 102 is substantially continuously interconnected via a plurality of struts 108.

Furthermore, at least one of the plurality of struts 108 may be a load-bearing strut.

Figures 2A, 2B, 2C:
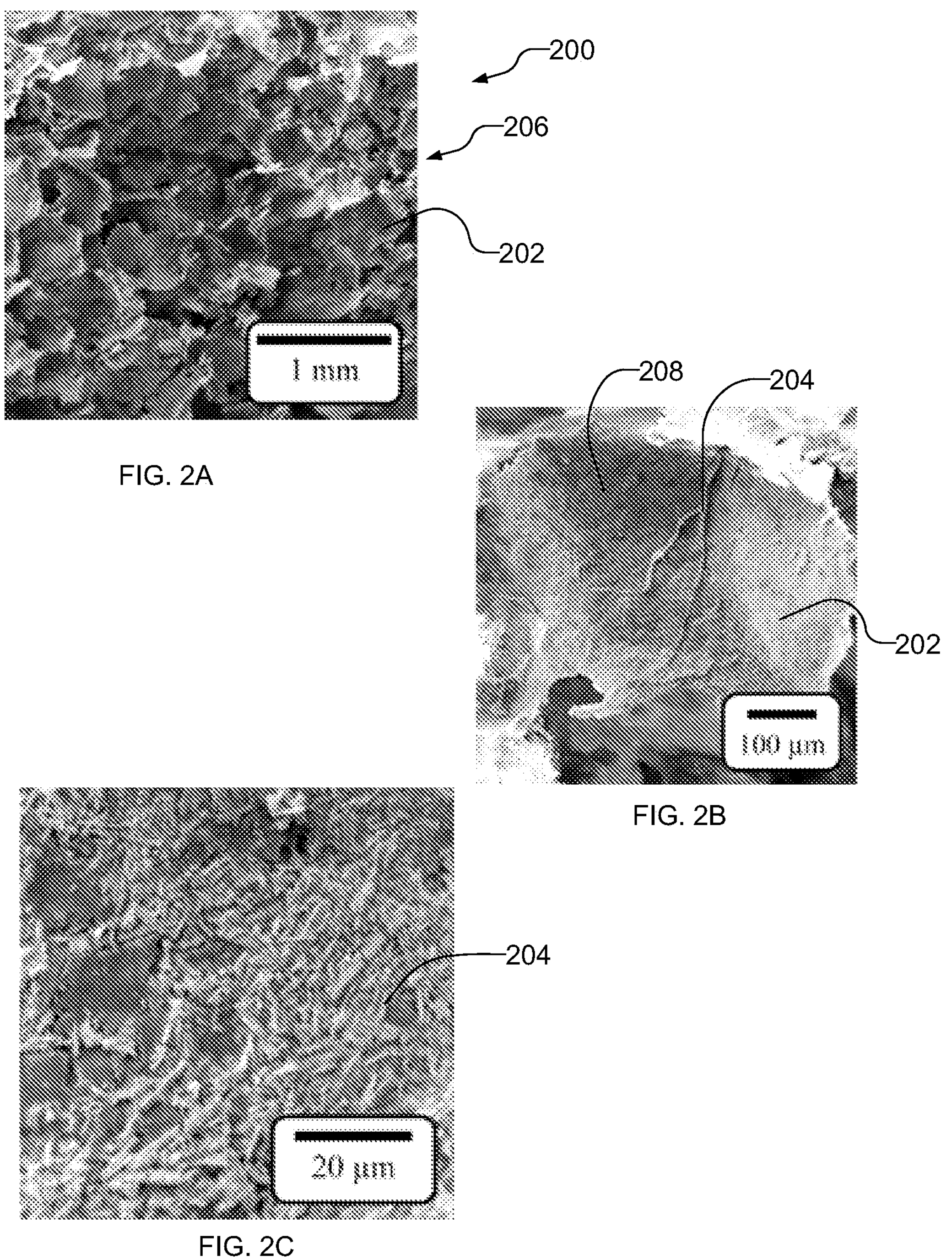
FIG. 2A-2C are scanning electron micrographs of a portion of the example porous composite material shown in increasing magnification.

FIGS. 2A-2C are scanning electron micrographs showing increasing magnification of a portion of an example scaffold 200 with struts 202. The example scaffold 200 is a PEEK scaffold reinforced with 40% by volume HA whiskers 204. FIG. 2A illustrates the architecture or matrix 206 of the scaffold 200 and FIG. 2B illustrates an enlarged portion of the struts 202. In the illustrated example, the HA whiskers 204 are integrally formed and/or embedded within the matrix 206 of the scaffold 200 for reinforcement. The HA whiskers 204 are also exposed on a surface 208 of the matrix of the scaffold 200 for bioactivity and/or bioresorption, as noted above. As shown in FIG. 2C, the HA whiskers 204 are aligned in a sheet texture and are exposed on the surface 208 of the struts 202.

The thermoplastic polymer of the example scaffolds described herein may be a biodegradable polymer for synthetic bone graft substitute applications, or nonbiodegradable for implant fixation applications. The thermoplastic polymer includes a continuous matrix of a composite material and is biocompatible and/or bioresorbable as described above.

Additionally, or alternatively, the polymer may be a radiolucent polymer, bioresorbable (i.e., a material capable of being resorbed by a patient under normal physiological conditions) and/or non-bioresorbable, as desired. Further, the thermoplastic polymer matrix may include a polymer suitable for injection via percutaneous or surgical injection so that the composite material 100 cures in vivo.

Suitable non-resorbable polymers include, without limitation, polyaryletherketone (PAEK), polyetheretherketone (PEEK), polyetherketonekteone (PEKK), polyetherketone (PEK), polyethylene, high density polyethylene (HDPE), ultra-high molecular weight polyethylene (UHMWPE), low density polyethylene (LDPE), polyethylene oxide (PEO), polyurethane, polypropylene, polypropylene oxide (PPO), polysulfone, polypropylene, copolymers thereof, and blends thereof. Suitable bioresorbable polymers include, without limitation, poly(DL-lactide) (PDLA), poly(L-lactide) (PLLA), poly(glycolide) (PGA), poly(□-caprolactone) (PCL), poly(dioxanone) (PDO), poly(glyconate), poly(hydroxybutyrate) (PHB), poly(hydroxyvalerate (PHV), poly (orthoesters), poly(carboxylates), poly(propylene fumarate), poly(phosphates), poly(carbonates), poly(anhydrides), poly (iminocarbonates), poly(phosphazenes), copolymers thereof, and blends thereof. Suitable polymers that are injectable via percutaneous or surgical injection that cure in vivo include, without limitation, polymethylmethacrylate (PMMA), and other polyacrylics from monomers such as bisphenol a hydroxypropylmethacrylate (bis-GMA) and/or tri (ethylene glycol) dimethacrylate (TEG-DMA).

Figure 3:
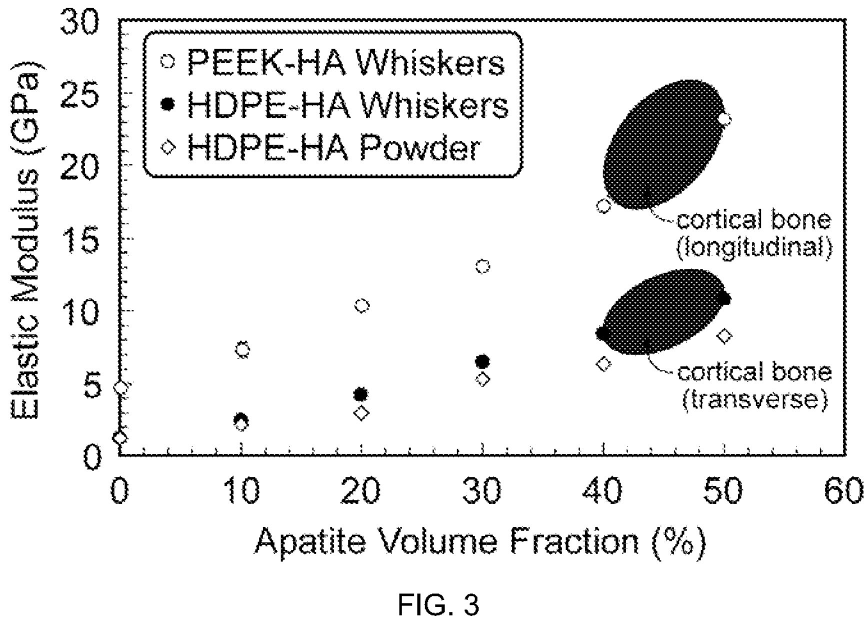
FIG. 3 is graphical representation of the elastic modulus of example apatite reinforced polymer composites versus the reinforcement volume fraction.

Although synthetic substitute composite materials made of polymers satisfy the functional criteria of an implantable device because they are, for example, formable and inexpensive, polymers alone lack biological efficacy to promote bone growth and/or may lack requisite mechanical properties to support load levels. To increase the mechanical properties of the polymers, the polymers are reinforced with calcium phosphates. The aspect ratio, size, volume fraction and degree of preferred orientation of the calcium phosphate particles 104 (e.g., HA whisker particles) may be tailored for the desired material properties and implant performance. For example, consider the information presented in FIG. 3, which is a graphical illustration of the elastic modulus of HA whisker and powder reinforced polymer composite materials versus the volume fraction percentage of the apatite calcium phosphates that is mixed with the polymer matrix. The shaded areas of FIG. 3 show approximate regions for the given mechanical property of the human cortical bone tissue. As depicted in the graph, the elastic modulus of the composite materials increases with increasing HA content. In addition, increasing the level of HA reinforcement in polymer composites increases cellular activity during osteointegration.

The calcium phosphate reinforcement particles 104 may be in the form of single crystals or dense polycrystals but are at least in some portion anisometric. "Anisometric" refers to any particle morphology (shape) that is not equiaxed (e.g., spherical), such as whiskers, plates, fibers, etc. Anisometric particles are usually characterized by an aspect ratio. For example, HA single crystals are characterized by the ratio of dimensions in the c- and a-axes of the hexagonal crystal structure. Thus, the anisometric particles in the present disclosure have an aspect ratio greater than 1. In one example, the mean aspect ratio of the reinforcement particles is from about 1 to about 100. By further example, the reinforcement particles can be provided in an amount of from about 1% by volume of the composite biomaterial to about 60% by volume, and for example, from about 20% by volume of the composite to about 50% by volume.

Figure 4:
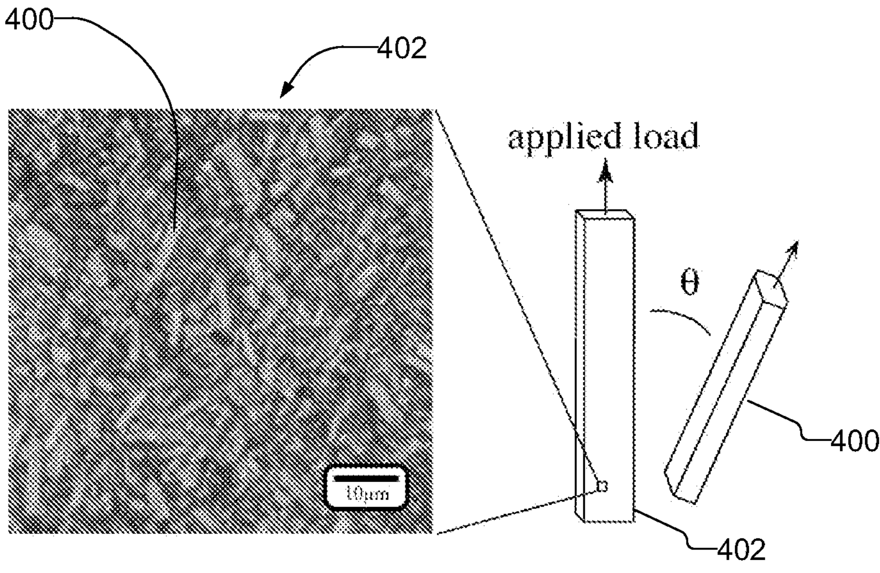
FIG. 4 shows scanning electron micrograph of a portion of the surface of an example composite material reinforced with calcium phosphate whiskers embedded within and exposed on the surface, and schematically showing the orientation of the whiskers relative to the loading direction of the material or scaffold strut.

Due to their morphology, the calcium phosphate reinforcements particles 104 may be oriented in bulk or near the surface of the polymer matrix 102 to provide directional properties, if desired. For example, if the reinforcement particles 104 are predominately aligned within the matrix 102 the morphological alignment of the particles 104 provides anisotropy for the overall composite 100, which can be tailored to be similar to the anisotropic mechanical properties of bone tissues. For example, FIG. 4 shows a micrograph of anisometric calcium phosphate reinforcement 400 on the surface of a dense composite polymer matrix 402. Also shown in FIG. 4 is a schematic illustration of a portion of matrix 402 and illustratively showing the orientation of the reinforcement particles 400 relative to the loading direction of the material and/or a scaffold strut, which is, for example, at an angle θ.

Furthermore, there are no limits on the size or amount of the calcium phosphate particles 104 in matrix 102, provided that the calcium phosphate particles 104 are dispersed within and/or exposed at the surface of the polymer matrix 102. For example, the reinforcement particles 104 may have a maximum dimension from about 20 nm to about 2 mm, and for example, between 20 nm to about 100 μm. While both nano- and micro-scale calcium phosphate particles improve the mechanical properties of the example synthetic composite material 100 described herein, nano-scale calcium phosphate particles are particularly effective for enhancing bioresorbability and cell attachment, and micro-scale particles are particularly effective for obtaining a uniform dispersion within the matrix 102.

Suitable calcium phosphates may include, without limitation, calcium HA, HA whiskers, HA, carbonated calcium HA, beta-tricalcium phosphate (beta-TCP), alpha-tricalcium phosphate (alpha-TCP), amorphous calcium phosphate (ACP), octacalcium phosphate (OCP), tetracalcium phosphate, biphasic calcium phosphate (BCP), anhydrous dicalcium phosphate (DCPA), dicalcium phosphate dihydrate (DCPD), anhydrous monocalcium phosphate (MCPA), monocalcium phosphate monohydrate (MCPM), and combinations thereof.

As described above, a synthetic composite material 100 not only bears physiological levels of load, but also promotes oseteointegration—the direct structural and functional connection between the living bone and the surface of the load-bearing implant. The bioactive calcium phosphate particles 104 (e.g., HA whiskers) exposed on the surface of the example porous matrix 102 promote a stable bone-implant interface. Osteointegration also requires the vascularization and growth of bone into an implant via interconnected and/or continuous porosity.

Figure 6:
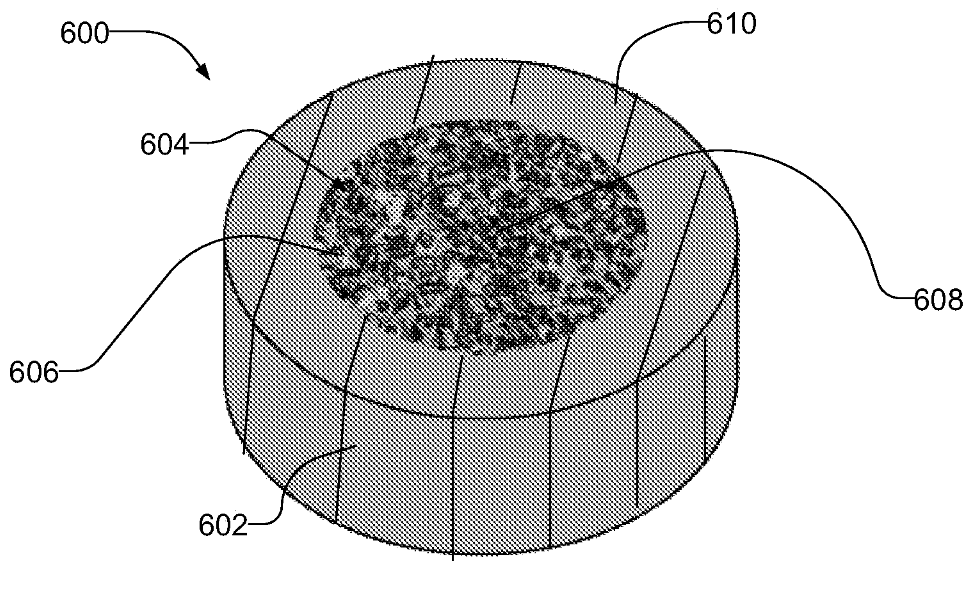
FIG. 6 illustrates another example scaffold described herein.
Figure 7:
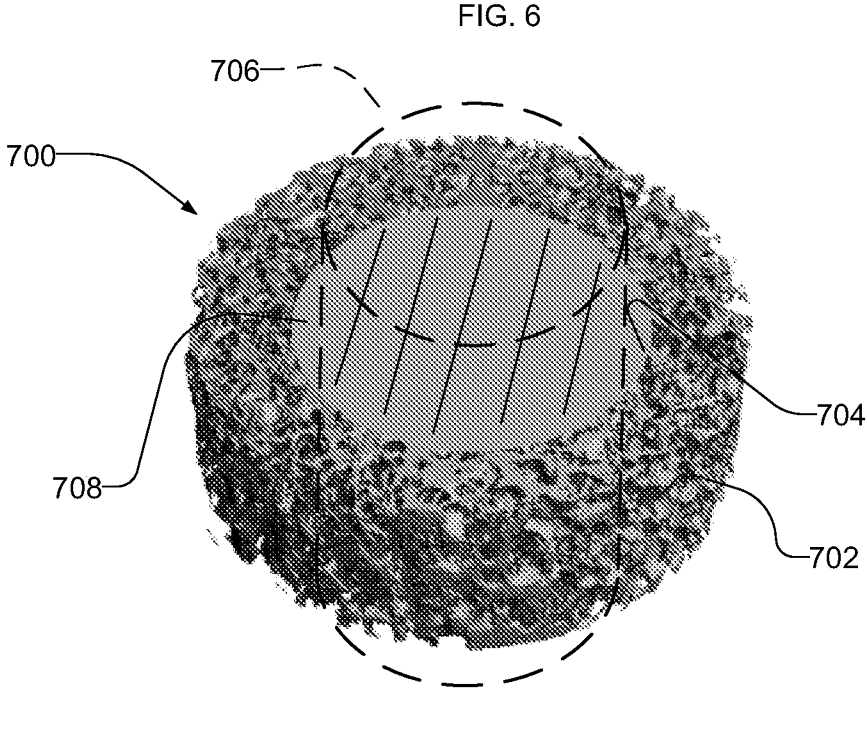
FIG. 7 illustrates yet another example scaffold described herein.

Thus, the size, volume fraction, shape, and directionality of the void spaces and/or pores 106 may be tailored to optimize osteoconduction and implant mechanical properties. The pores 106 may be any size or shape, while maintaining a continuous network to promote a fusion through the formation of new bone tissue in the void spaces and/or pores 106. For example, the pores 106 may be present throughout the matrix 102 as illustrated in FIG. 1A. Also, the pores 106 may be functionally graded in any material or implant direction, for example, radially, as shown in FIGS. 6 and 7, from a highly porous region to a relatively dense region or may include a void space. The change in porosity from one region to another may be very distinct, for example as shown in FIGS. 6 and 7, or gradual. Furthermore, the graded change may be uniform or variant. In addition, instead of a graded change there may be a combination of materials having two or more densities of pores. The central void may be any shape or size, and may receive (e.g., be filled) a material, a structure, or the composite material 100 (i.e., the composite material graded from the porous outer surface to a dense center), thereby forming a porous outer perimeter and a dense central region. Examples are further described in connection with FIGS. 6 and 7 below.

As discussed in greater detail below, the porosity and/or pore sizes 106 may be selectively formed by the inclusion of, for example, a porogen material during synthesis of the composite material 100. Pores spaces may range from about 100 μm to about 500 μm, and, for example, from about 250 μm to about 500 μm. The example composite biomaterial 100 may additionally contain some fraction of microporosity within scaffold struts that is less than about 10 μm in size. The total amount of porosity within porous regions may range from about 1% to about 90% by volume, and, for example, between about 70% and 90% by volume. However, the porosity may also be tailored via other processes such as, for example, microsphere sintering, fiber weaving, solvent casting, electrospinning, freeze drying (lyophilization), thermally induced phase separation, gas foaming, and rapid prototyping processes such as, for example, solid freeform fabrication, robotic deposition (aka, robocasting), selective laser sintering, fused deposition modeling, three-dimensional printing, laminated object manufacturing, stereolithography, etc., or any other suitable process(es) or combination(s) thereof.

Additionally, the example composite material 100 may optionally include additives, if desired. For example, the composite material 100 may include one or more surface-active agents to enhance interfacial bonding between the reinforcement particles 104 and the polymer matrix 102. The void spaces and/or pores 106 may accommodate and deliver one or more growth factors such as, for example, BMP, to enhance osteoinductivity and/or bone regeneration. Furthermore, the void spaces and/or pores 106 may also accommodate and deliver one or more transcription factors, matrix metalloproteinases, peptides, proteins, bone cells, progenitor cells, blood plasma, bone marrow aspirate, or combinations thereof, to improve or speed bone regeneration, or resorption and replacement of the biomaterial. In some examples, the void spaces and/or pores 106 may further accommodate a carrier material that may be incorporated into the void spaces and/or pores 106. The carrier material may include, for example, a collagen sponge, membrane, or a hydrogel material to deliver the growth factor material such as, for example, the BMP. The calcium phosphate reinforcements 104 exposed on the surface of the porous matrix 102, along with the porosity, improves the retention of the BMP within the matrix 102 and at the peri-implant interface.

Figure 5A:
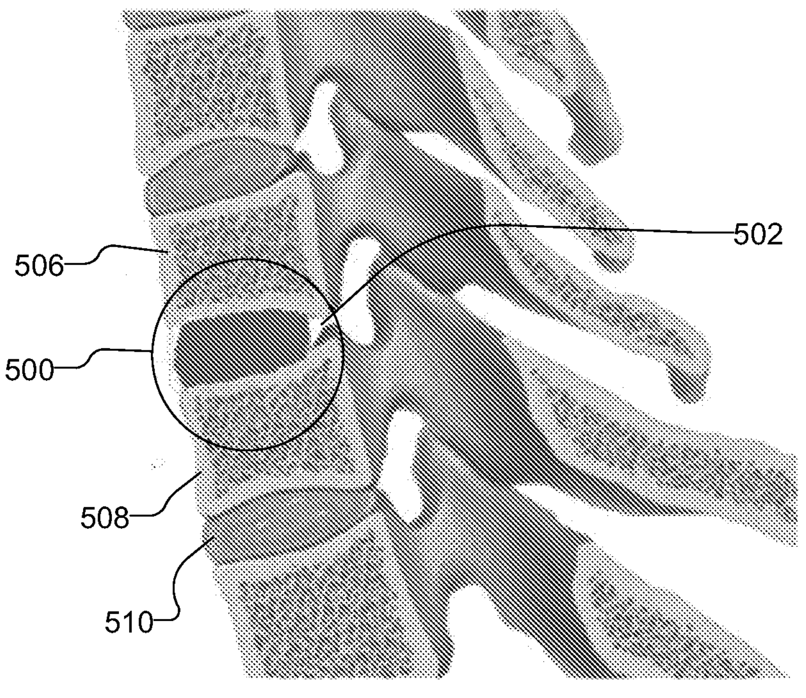
FIG. 5A is a schematic illustration of a known spinal fusion cage inserted between spinal vertebrae.

FIG. 5A is an illustration showing a known interbody spinal fusion cage 500. The example spinal fusion cage 500 is implanted in the inter-vertebral space 502 between two adjacent vertebrae 506 and 508. A disc 510, due to degeneration, herniation, etc., is typically removed and replaced by the spinal fusion cage 500. The spinal fusion cage 500 is used to support or restore vertebral height, and, thus, stabilize or retain adjacent vertebrae 506 and 508 in a desired position. Additionally, the spinal fusion cage 500 is to promote fusion between the vertebrae 506 and 508.

Figure 5B:
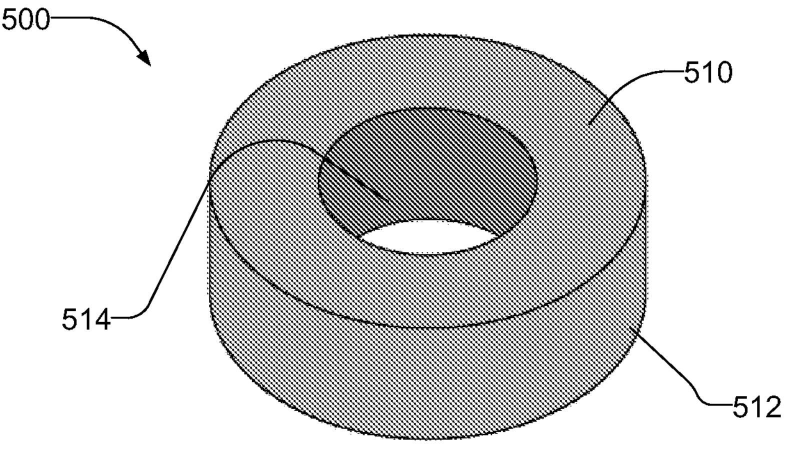
FIG. 5B illustrates the example known spinal fusion cage of FIG. 5A.

FIG. 5B is an enlarged illustration of the known spinal fusion cage 500 of FIG. 5A. A typical spinal fusion cage 500 includes a body 510 having a dense outer region 512 and a void 514 at its center. The dense outer surface 512 may be made of PEEK, titanium, or other material that can be used to support the vertebrae 506 and 508. However, the spinal fusion cage 500 made of a PEEK, titanium, etc., cannot attach to the bone. Thus, to promote bone ingrowth, the center void 514 is typically provided with a packing material (not shown) such as, a natural bone graft, a collagen sponge that retains bone growth factors, or the spinal fusion cage 500 is coated with the bone growth factors or other agents that promote osteoinduction.

The example porous scaffold 101 having the composite material 100 described herein, and with respect to FIG. 1A, can be implemented with the spinal fusion cage 500 of FIGS. 5A and 5B to replace the packing materials, such as natural bone graft. As noted above, the porous scaffold 101 promotes bone ingrowth and the pores 106 may accommodate or deliver for example, a BMP, to further improve rate of growth (fusion rate). Furthermore, the calcium phosphate (e.g., HA whisker) binds to the body 510 and localizes the BMP within the central void 514, which further promotes osteointegration.

FIG. 6 illustrates another example scaffold or matrix 600 implemented with the example composite material 100 described herein. The example scaffold 600 may be implemented as an interbody spinal fusion cage. The scaffold 600 includes a body 602 having a porous polymer matrix 604 integrally formed or embedded with anisometric calcium phosphate particles 606. Furthermore, the matrix 604 of the example scaffold 600 includes a radiolucent polymer (e.g., PEEK) integrally formed or embedded with anisometric calcium phosphate reinforcements 606 such as, for example, HA whiskers. The radiolucent polymer provides improved radiographic analysis of fusion following implantation. The example scaffold 600 may also include a BMP such as, for example, rhBMP-2. In another example, the example scaffold 600 is a biocompatible, microporous polymer scaffold or matrix supplemented with anisometric calcium phosphate reinforcements and BMP.

Additionally, the example scaffold 600 may formed so that the pores are functionally graded in any material or implant direction such as, for example, radially, as shown in FIG. 6, from a highly porous center or central region 608 to relatively dense outer region or surface 610. The change in porosity from one region to another may be distinct or gradual from the central region 608 to the outer region 610. Further, the graded change may be uniform or variant. The dense outer region 610 provides structural integrity along with the advantages of the composite material 100 described herein. In the illustrated example, the porous structure 604 has pore sizes that range between about 100 μm and about 500 μm, and preferably, between about 250 μm and about 500 μm, and a porosity that ranges between about 1% to about 90%. Furthermore, the spinal fusion cage material 600 may include microporosity having pore sizes less than about 10 μm.

FIG. 7 illustrates another example scaffold 700. The porous scaffold 700 includes a porous matrix 702 having the composite material 100 described herein. The porous scaffold 700 includes a center or central void 704 that may be any shape or size. Additionally, or alternatively, the central void 704 may receive a material 706, a stem, or any other substance or structure, illustratively depicted by dashed lines. For example, the central void 704 may receive a stem 706 (e.g., an implant) such as, for example, a titanium stem, a dense composite stem (e.g., a PEEK composite stem), or any other suitable material or structure.

Additionally, in other examples, the scaffold 700 is formed so that the pores are functionally graded in any material or implant direction, for example, radially as shown in FIG. 7, from a high porous outer region or surface 702 to a relatively dense center or central region 708. The change in porosity from one region to another may be distinct or gradual from the central region 708 to the highly porous outer region 702. Further, the graded change may be uniform or variant. In this manner, the example scaffold 700 forms a porous perimeter having a dense core, where the material is continuous from the porous perimeter to the dense core. The dense central region 708 provides structural integrity along with the advantages of the composite material 100 described herein. In the illustrated example, the porous matrix 702 and the dense central region 708 may have pore sizes that range between about 100 μm and about 500 μm, and preferably, between about 250 μm and about 500 μm, and a porosity that ranges between about 1% to about 90%. Furthermore, the spinal fusion cage 700 may include a microporosity having pore sizes less than about 10 μm.

In other examples, the composite material 100 and/or the scaffolds 101, 600, 700 may also include a roughened surface such as, for example, serrated teeth, that come into direct contact with the adjacent peri-implant tissue to prevent movement relative to the peri-implant tissue after implantation. Additionally, or alternatively, although not shown, the scaffolds 101, 600, 700 may include holes, notches, pins, radiographic markers, or other features that may be gripped or otherwise used for positioning of the scaffolds 101, 600, 700 by minimally invasive surgical tools and procedures.

The example composite material 100 and/or the scaffolds 101, 600, 700 may be manufactured by methods common to reinforced thermoplastic and thermosetting polymers, including but not limited to injection molding, reaction injection molding, compression molding, transfer molding, extrusion, blow molding, pultrusion, casting/potting, solvent casting, microsphere sintering, fiber weaving, solvent casting, electrospinning, freeze drying (lyophilization), thermally induced phase separation, gas foaming, and rapid prototyping processes such as solid freeform fabrication, robotic deposition (aka, robocasting), selective laser sintering, fused deposition modeling, three-dimensional printing, laminated object manufacturing, stereolithography, etc., or any other suitable process(es) or combination(s) thereof.

Figure 8:
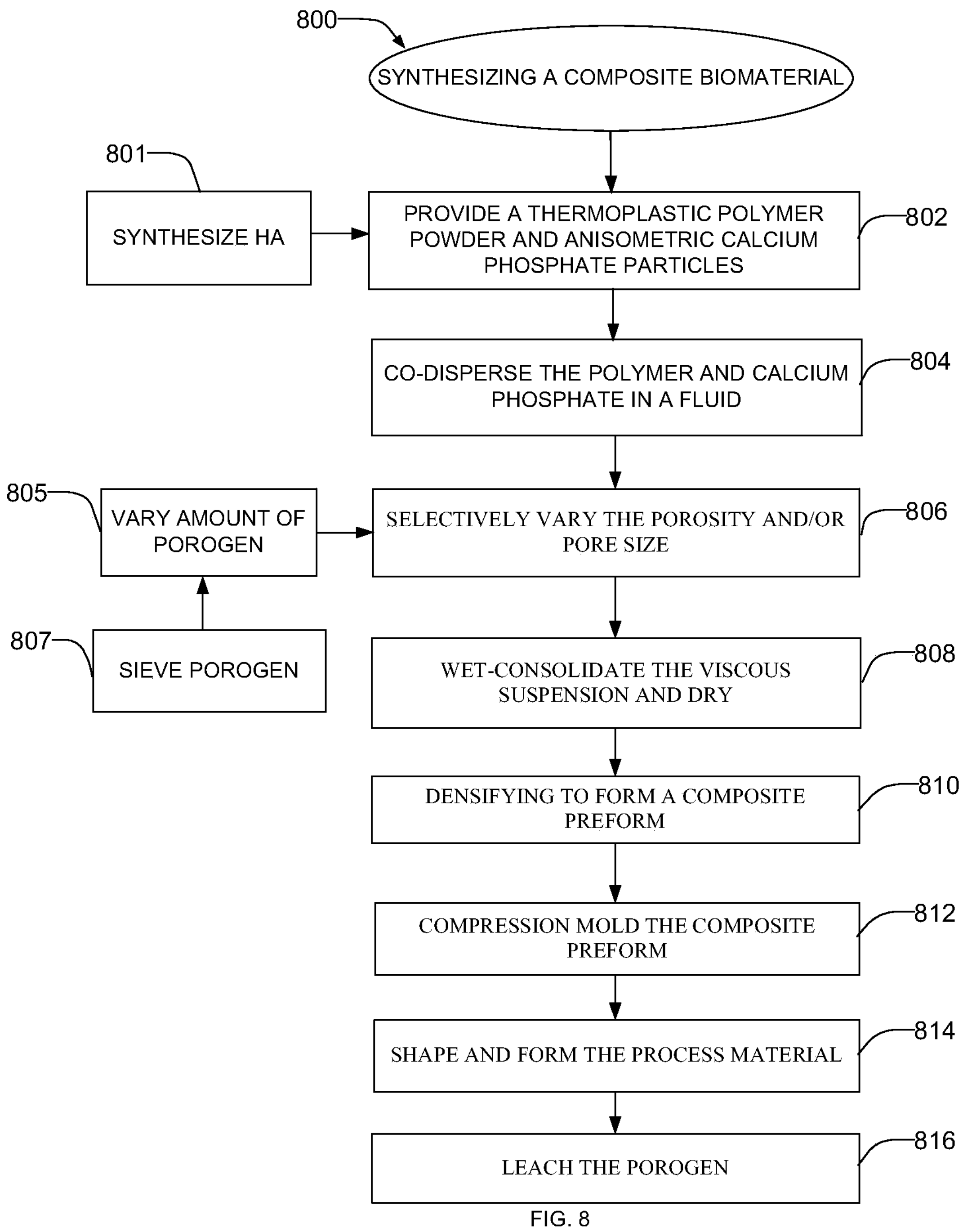
FIG. 8 is a flow diagram illustrating an example process of creating an example composite material apparatus described herein.

FIG. 8 is a flowchart of an example method 800 that may be used to synthesize the example composite material 100 and/or scaffolds 101, 600, 700 described herein. While an example manner of synthesizing the example composite material 100 and/or scaffolds 101, 600, 700 has been illustrated in FIG. 8, one or more of the steps and/or processes illustrated in FIG. 8 may be combined, divided, re-arranged, omitted, eliminated and/or implemented in any other way. Further still, the example method of FIG. 8 may include one or more processes and/or steps in addition to, or instead of, those illustrated in FIG. 8, and/or may include more than one of any or all of the illustrated processes and/or steps. Further, although the example method is described with reference to the flow chart illustrated in FIG. 8, persons of ordinary skill in the art will readily appreciate that many other methods of synthesizing the example composite material 100 and/or scaffolds 101, 600, 700 may alternatively be used.

The composite material 100 and/or the scaffolds 101, 600, 700 are processed using a powder processing approach in conjunction with compression molding and particle leaching techniques and is particularly suited for achieving a high concentration (e.g., >40 vol %) of well-dispersed (and aligned, if desired) anisometric calcium phosphate reinforcements (e.g., HA whiskers) in a thermoplastic matrix (e.g., PEEK) with minimal degradation of the calcium phosphate size/shape during processing. In this manner, the calcium phosphate reinforcement volume fraction, aspect ratio, size and orientation; the polymer; and the size, volume fraction, shape and directionality of the void space and/or porosity may be tailored to vary the mechanical properties of the composite material 100 and/or scaffolds 101, 600, 700.

A polymer such as, for example, PEEK, and anisometric calcium phosphate particles, such as HA whiskers, are provide in powder form (block 802). The PEEK polymer powder may have, for example, a mean particle size of about 26 μm. The HA whiskers may be synthesized (block 801) using, for example, the chelate decomposition method.

The PEEK powder and the synthesized HA whiskers are co-dispersed in a fluid (block 804) such as, for example ethanol, and mixed (block 804) using, for example, ultrasonication under constant stirring—forming a viscous suspension.

After the polymer powder and the HA whiskers are mixed, the porosity of the mixture is selectively varied and/or tailored (block 806). In one example, the porosity may be formed and tailored by the addition of a suitable porogen material such as, for example, NaCl, wax, polysaccharides (sugars), cellulose, etc. The extent of the porosity can be controlled by varying the amount of porogen used (block 805), while the pore size could be tailored by sieving the porogen (block 807) to a desired size prior to mixing the porogen with the polymer mixture. In another examples, the porosity and/or the pore size of the polymer matrix may be selectively varied using any other suitable methods and/or process(es) such as, for example, microsphere sintering, fiber weaving, solvent casting, electrospinning, freeze drying (lyophilization), thermally induced phase separation, gas foaming, or rapid prototyping processes such as, for example, solid freeform fabrication, robotic deposition (aka, robocasting), selective laser sintering, fused deposition modeling, three-dimensional printing, laminated object manufacturing, stereolithography, etc., or any other suitable process(es) or combination(s) thereof.

The viscous suspension is wet-consolidated (block 808) by, for example, vacuum filtration and drying to remove any residual fluid (i.e., ethanol). The composite mixture is densified (block 810) by, for example, uniaxial compression, to form a composite preform.

Following the initial densification, the preform is compression molded (block 812) and/or sintered at elevated temperatures (e.g., approximately 20° C. to 400° C.) sufficient to fuse the polymer particles with minimal damage to the calcium phosphate reinforcements. The process or composite material may be heated to a desired processing temperature and the implant may be shaped or formed (block 814). Densifying and molding the composite material includes aligning the calcium phosphate reinforcement particles (e.g., HA whiskers) morphologically and/or crystallographically within the scaffold struts.

The scaffold may have any shape and/or size (e.g., any polygonal shape) and can be formed by methods common to reinforced thermoplastic and thermosetting polymers, including but not limited to injection molding, reaction injection molding, compression molding, transfer molding, extrusion, blow molding, pultrusion, casting/potting, solvent casting, and rapid prototyping processes such as, for example, solid freeform fabrication, robotic deposition (aka, robocasting), selective laser sintering, fused deposition modeling, three-dimensional printing, laminated object manufacturing, stereolithography, etc., or any other suitable process(es). The composite material 100 and/or the scaffolds 101, 600, 700, are formed by the mold walls and/or machining after molding.

The composite material undergoes a leaching process (block 816) to remove, for example, the porogen used during synthesis of the composite material. The leaching may occur, for example, via a dissolution method, heating method, and/or any other suitable methods and/or process(es). More specifically, dissolution may include immersing the scaffold in a fluid, such as, for example, deionized water.

Furthermore, viscous flow of the polymer/reinforcement mixture during molding can be designed to tailor the preferred orientation of the anisometric reinforcements in the implant. Additionally, surface-active agents may be added during the mixing process and/or to the surface of the composite material to enhance interfacial bonding between reinforcement particles and the matrix.

The following example is provided to further illustrate the example apparatus and methods described herein and, of course, should not be construed as in any way limiting in scope. It is to be understood by one of ordinary skill in the art that the following examples are neither comprehensive nor exhaustive of the many types of methods and apparatus which may be prepared in accordance with the present disclosure.

In the example, commercially available PEKK and sodium chloride (NaCl) powders with mean particle sizes of 70 and 250 μm, respectively, were used as-received. HA whiskers were synthesized using the chelate decomposition method. The as-synthesized HA whiskers were measured by optical microscopy to have a mean length of 21.6 μm, width of μm and aspect ratio of 7.6.

In the example, composite scaffolds with 75, 82.5 and 90% porosity were processed with 0-40 vol % HA whisker reinforcement. Appropriate amounts of polymer powder and HA whiskers were co-dispersed in ethanol via a sonic dismembrator and mechanical stirring at 1200 rpm. Following dispersion, the appropriate amount of the NaCl (i.e., porogen) was added to the suspension and mixed by hand using a Teflon coated spatula. The total scaffold volume consisted of the material volume plus the pore volume. Thus, the reinforcement level was calculated based the desired material volume, while the porosity level was calculated based on the total scaffold volume. After mixing, the viscous suspension was wet-consolidated using vacuum filtration. The powder mixture was dried overnight in a forced convection oven at 90° C. and densified at 125 MPa in a cylindrical pellet die using a hydraulic platen press. The die and densified powder mixture was heated in a vacuum oven to the desired processing temperature and transferred to a hydraulic platen press for compression molding. Scaffolds with 82.5 and 90% porosity were molded at 350° C., while scaffolds with 75% porosity were molded at 350, 365 and 375° C. A pressure of 250 MPa was applied to the die as the polymer solidified. After cooling to room temperature, the sintered composite pellet was ejected from the die and placed approximately 300 mL deionized water for at least 72 h to dissolve the NaCl crystals. The deionized water was changed daily. The as-molded composite scaffolds had a diameter of 1 cm and were machined to a height of 1 cm.

In the example, un-confined compression tests were performed to investigate the mechanical properties of the composite scaffolds. Specimens were tested on an electromagnetic test instrument in phosphate buffered saline (PBS) at 37° C. using a crosshead speed of 1 mm/min. Force-displacement data was used to calculate the clastic modulus, compressive yield stress (CYS), and failure strain of the composite scaffolds. One-way analysis of variance (ANOVA) was used to compare mechanical properties between experimental groups. The compressive properties of HA whisker reinforced PEKK scaffolds were tabulated in table 1.

The table below provides mechanical properties of the example PEKK scaffold reinforced with HA whiskers that was processed using a compression molding/particle leaching method such as, for example, the method 800 of FIG. 8 as implemented in the description above. The mechanical properties of HA whisker reinforced PEKK were evaluated in uniaxial compression. Tensile properties of the HA whisker reinforced PEKK scaffolds were evaluated prior to scaffold fabrication.

TABLE 1

| Porosity (%) | HA Content (Vol %) | Molding Temperature (° C.) | Elastic Modulus (MPa) | CYS (MPa) | Yield Strain (%) |
|---|---|---|---|---|---|
| 75 | 0 | 350 | 69.5 (12.2) | 1.25 (0.16) | 5.7(0.4) |
| 75 | 0 | 365 | 100.7 (10.7) | 2.04 (0.26) | 4.4(1.2) |
| 75 | 0 | 375 | 95.6 (10.5) | 2.55 (0.34) | 4.4(1.1) |
| 75 | 20 | 350 | 106.3 (15.0) | 1.28 (0.13) | 3.7(1.1) |
| 75 | 20 | 365 | 115.4 (13.4) | 1.77 (0.30) | 2.9(0.6) |
| 75 | 20 | 375 | 141.1 (39.2) | 2.28 (0.35) | 2.9(0.7) |
| 75 | 40 | 350 | 54.0 (18.3) | 0.52 (0.17) | 2.2(0.3) |
| 75 | 40 | 365 | 84.3 (41.5) | 1.15 (0.38) | 2.7(0.5) |
| 75 | 40 | 375 | 120.2 (29.8) | 1.65 (0.34) | 2.3(1.9) |
| 82 | 40 | 350 | 15.7 (6.7) | 0.13 (0.03) | 2.6(1.9) |
| 90 | 0 | 350 | 0.75 (0.18) | 0.15 (0.04) | 30(0.0) |
| 90 | 40 | 350 | 0.23 (0.13) | 0.04 (0.01) | 30(0.0) |

As shown in the table, for a given reinforcement level, the compressive modulus decreased with increased porosity, and the yield strength decreased with increased porosity. Scaffolds with 0% vol % HA whisker reinforcement and 75% and 90% porosity exhibited moduli of 69.5 and 0.75 MPa, while scaffolds with 40 vol % HA whisker reinforcement and 75%, 82% and 90% porosity exhibited moduli of 54.0, 15.7 and 0.23 MPa, respectively.

Scaffolds with 0 vol % HA whisker reinforcement and 75% and 90% porosity exhibited yield strengths of 1.25 MPa and 0.15 MPa, respectively. Scaffolds with 40 vol % HA whisker reinforcement and 75%, 82% and 90% porosity exhibited yield strengths of 0.52 MPa, 0.13 M P a and 0.04 MPa, respectively. The HA content also affected the modulus and failure strain of the scaffolds. A scaffold having 75% porosity and 20 vol % reinforcement HA whisker exhibited modulus of 106.3 MPa, compared to a modulus of 69.5 MPa for scaffolds with 0 vol % HA whisker reinforcement.

The example methods and apparatus described herein offer synthetic porous composite material that may be used for synthetic bone substitutes for implant fixation, fraction fixation, synthetic bone graft substitutes, interbody spinal fusion, tissue engineering scaffolds, or other applications. Many aspects of the of the porous composite material may be tailored to provide specific mechanical, biological, and surgical functions, such as, the polymer composition and molecular orientation, porosity and pore size of the porous matrix, or the HA reinforcement content, morphology, preferred orientation, and size.

Although the teachings of the present disclosure have been illustrated in connection with certain examples, there is no intent to limit the present disclosure to such examples. On the contrary, the intention of this application is to cover all modifications and examples fairly falling within the scope of the appended claims either literally or under the doctrine of equivalents.

What we claim is:

1. A porous reinforced composite scaffold, comprising:

a thermoplastic polymer matrix comprising:

a plurality of reinforcement particles; and a substantially continuously interconnected plurality of pores disposed in a first portion of the thermoplastic polymer matrix such that the first portion is porous and a second portion of the thermoplastic polymer matrix is dense, wherein;

the thermoplastic polymer matrix and the plurality of reinforcement particles define a material volume of the scaffold;

the plurality of pores define a pore volume of the scaffold;

each of the pores in the plurality of pores is defined by voids interconnected by struts; and at least a portion of the plurality of reinforcement particles are exposed on the struts within the pore voids.

2. The porous reinforced composite scaffold according to claim 1, wherein the thermoplastic polymer matrix comprises a polymer selected from the group consisting of polyaryletherketone (PAEK), polyetheretherketone (PEEK), polyetherketonekteone (PEKK), polyetherketone (PEK), polyethylene, high density polyethylene (HDPE), ultra-high molecular weight polyethylene (UHMWPE), low density polyethylene (LDPE), polyethylene oxide (PEO), polyurethane, polypropylene, polypropylene oxide (PPO), polysulfone, polypropylene, copolymers thereof, and combinations thereof.

3. The porous reinforced composite scaffold according to claim 1, wherein the thermoplastic polymer matrix comprises a polyaryletherketone (PAEK) polymer selected from the group consisting of polyetheretherketone (PEEK), polyetherketonekteone (PEKK), and polyetherketone (PEK).

4. The porous reinforced composite scaffold according to claim 1, wherein the plurality of reinforcement particles are present in the first portion of the thermoplastic polymer matrix from about 1% to about 60% of the material volume and are distributed essentially uniformly throughout the first portion of the thermoplastic polymer matrix.

5. The porous reinforced composite scaffold according to claim 1, wherein the plurality of reinforcement particles comprise particles having a morphology that is either equiaxed, or non-equiaxed having a mean aspect ratio of greater than 1 and less than 100, and wherein the size of the plurality of reinforcement particles ranges between 20 nm and 2 mm in a largest dimension.

6. The porous reinforced composite scaffold according to claim 1, wherein the plurality of reinforcement particles comprise particles that are spherical, whiskers, plates, fibers, or combinations thereof.

7. The porous reinforced composite scaffold according to claim 1, wherein the plurality of reinforcement particles are selected from the group consisting of hydroxyapatite, calcium-deficient hydroxyapatite, carbonated calcium hydroxyapatite, beta-tricalcium phosphate (beta-TCP), alpha-tricalcium phosphate (alpha-TCP), amorphous calcium phosphate (ACP), octacalcium phosphate (OCP), tetracalcium phosphate, biphasic calcium phosphate (BCP), anhydrous dicalcium phosphate (DCPA), dicalcium phosphate dihydrate (DCPD), anhydrous monocalcium phosphate (MCPA), monocalcium phosphate monohydrate (MCPM), and combinations thereof.

8. The porous reinforced composite scaffold according to claim 1, wherein the thermoplastic polymer matrix comprises a polyaryletherketone (PAEK) polymer, and wherein the plurality of reinforcement particles comprises anisometric calcium phosphate particles.

9. The porous reinforced composite scaffold according to claim 1, wherein the pore volume of the first portion ranges from about 1% to about 95%, by volume, based on the scaffold volume, and wherein each of the pores in the plurality of pores is either homogenous or heterogeneous in shape and is either homogeneous or heterogeneous in size in a range from about 10 μm to about 500 μm.

10. The porous reinforced composite scaffold according to claim 1, wherein the first portion is an outer perimeter of the porous reinforced composite scaffold and the second region is a central region of the porous reinforced composite scaffold.

11. The porous reinforced composite scaffold according to claim 1, wherein the first portion is a central region of the porous reinforced composite scaffold and the second region is an outer perimeter of the porous reinforced composite scaffold.

12. The porous reinforced composite scaffold according to claim 1, wherein the porosity within the first portion of the porous reinforced composite scaffold is uniform.

13. The porous reinforced composite scaffold according to claim 1, wherein the porosity within the first portion of the porous reinforced composite scaffold varies.

14. The porous reinforced composite scaffold according to claim 1, wherein the first portion of the porous reinforced composite scaffold has a compressive elastic modulus of trabecular bone.

15. A porous reinforced composite scaffold, comprising:

a thermoplastic polymer matrix comprising:

a plurality of reinforcement particles; and a substantially continuously interconnected plurality of pores disposed in a first portion of the thermoplastic polymer matrix such that the first portion is porous and a second portion of the thermoplastic polymer matrix is dense, wherein:

the thermoplastic polymer matrix and the plurality of reinforcement particles define a material volume of the scaffold;

the plurality of pores define a pore volume of the scaffold;

each of the pores in the plurality of pores is defined by voids interconnected by struts;

at least a portion of the plurality of reinforcement particles are exposed on the struts within the pore voids;

the plurality of reinforcement particles are non-equiaxed and are present in the first portion of the thermoplastic polymer matrix from about 1% to about 60% of the material volume; and each of the pores in the plurality of pores is defined by voids interconnected by struts and has a size within a range from about 10 μm to about 500 μm.

16. The porous reinforced composite scaffold according to claim 15, wherein the first portion is an outer perimeter of the porous reinforced composite scaffold and the second region is a central region of the porous reinforced composite scaffold.

17. The porous reinforced composite scaffold according to claim 15, wherein the first portion is a central region of the porous reinforced composite scaffold and the second region is an outer perimeter of the porous reinforced composite scaffold.

18. The porous reinforced composite scaffold according to claim 15, wherein the thermoplastic polymer matrix comprises a polyaryletherketone (PAEK) polymer, and wherein the plurality of reinforcement particles comprises anisometric calcium phosphate particles.

19. The porous reinforced composite scaffold according to claim 18, wherein the porosity within the first portion of the porous reinforced composite scaffold is uniform.

20. The porous reinforced composite scaffold according to claim 18, wherein the porosity within the first portion of the porous reinforced composite scaffold varies.

* * * * *